United States Patent
Coombs

(10) Patent No.: US 6,752,790 B2
(45) Date of Patent: Jun. 22, 2004

(54) DOSAGE VESSEL FOR USE WITH AN INDWELLING FEEDING TUBE

(76) Inventor: Karla Coombs, 21 Union Turnpike, Branchville, NJ (US) 07826

( * ) Notice: Subject to any disclaimer, the term of this patent is extended or adjusted under 35 U.S.C. 154(b) by 0 days.

(21) Appl. No.: 10/086,071

(22) Filed: Feb. 27, 2002

(65) Prior Publication Data

US 2003/0163113 A1 Aug. 28, 2003

(51) Int. Cl.$^7$ ............................. A61M 5/14; A61B 19/00
(52) U.S. Cl. ........................................ 604/251; 604/405
(58) Field of Search ................................ 604/251, 259, 604/260, 409

(56) References Cited

U.S. PATENT DOCUMENTS

| | | | |
|---|---|---|---|
| 3,153,415 A | | 10/1964 | Sheridan |
| 3,857,392 A | * | 12/1974 | Ogle ........................... 604/91 |
| 4,335,770 A | * | 6/1982 | Kulle et al. .................. 604/408 |
| 4,601,701 A | | 7/1986 | Mueller, Jr. |
| 4,687,473 A | * | 8/1987 | Raines ........................ 604/251 |
| 5,071,405 A | | 12/1991 | Piontek et al. |
| RE34,365 E | * | 8/1993 | Theeuwes .................... 604/85 |
| 5,445,630 A | | 8/1995 | Richmond |
| 5,527,280 A | | 6/1996 | Goelz |
| 5,871,467 A | | 2/1999 | Reuning et al. |

OTHER PUBLICATIONS

Internet pages, Abbott Laboratories Feeding Tube Irrigation Adapter (2 pages).
Internet pages, Abbott Laboratories Gastrostomy Tubes (2 pages).
Internet pages, Abbott Laboratories Gravity Feeding Set (3 pages).
Internet pages, Abbott Laboratories Jejunal Feeding Tubes (2 pages).
Internet pages, Abbott Laboratories Nasoenteric Tubes (3 pages).
Internet pages, Abbott Laboratories Y–port Connectors (2 pages).
Internet pages, Abbott Laboratories Y–port Connector with Right Angle Adapter (2 pages).
Brochure— "Tube Feeding at Home for Nasogastric, Nasoduodenal, or Nasojejunal Tube Feeding", Ross Medical Nutritional System.
Internet pages– Ross Pump and Gravity Sets with Piercing Pin (2 pages).
Internet pages– Ross Enteral Pump Set with Piercing Pin (for Non–Ross Pumps) (2 pages).

* cited by examiner

Primary Examiner—Brian L. Casler
Assistant Examiner—Lina R. Kontos
(74) Attorney, Agent, or Firm—Muserlian, Lucas & Mercanti, LLP

(57) ABSTRACT

The present invention is an apparatus for intermittently providing oral medications to a patient being fed through a feeding tube, the apparatus having a dosage vessel, which preferably can be capped or sealed, and a secure fluid path to a tubing connector for connecting to the indwelling feeding tube.

23 Claims, 3 Drawing Sheets

DOSAGE VESSEL FOR USE WITH AN INDWELLING FEEDING TUBE

BACKGROUND OF THE INVENTION

People who are unable to eat or swallow regular food are provided with enteral feeding. The typical apparatus for enteral feeding comprises a single lumen tube structure, called a feeding tube, the distal end of which has aperatures for delivery of the enteral feeding solution to the stomach or small intestine. Some feeding tubes are threaded through the nasopharynx into the patient's stomach or small intestine. Others are placed through a stoma in the abdominal wall. The proximal end of the feeding tube is connected to a container of enteral feeding solution by a tubing set which is formed integrally with, or securely fastened to, the container. The feeding solution may be supplied in prefilled bags, or standing reservoir containers that may be filled on-site. It requires special training to place a feeding tube in a patient. Once the tube is properly in place, effort is taken to not dislodge it. Similarly, the feeding tube is not withdrawn or replaced until it is necessary to do so. Also, once the tube is in place, medications cannot be administered through the mouth.

Adding the medications to the feeding solution in the 250 ml. or more standing reservoir container of feeding solution, however, is not the answer. Adding medications to the feeding solution unnecessarily increases the time of administration of the medication. In addition, unless the medication is very thoroughly mixed with feeding solution, approximating the dosage of medications administered from the combined volumes of feeding solution and oral medications given is not only difficult to calculate, but also difficult to measure accurately, as the volume of medication is so much smaller than the volume of feeding solution. If the container of feeding solution is a tamper-proof container, it may be impossible to mix the oral medications with feeding solution. Indeed, the enteral feeding solution may be supplied in a tamper-proof container or bag, to provide a fixed, known, quantity and composition, as well as to prevent its alteration or contamination.

One can attempt to get the medication into the open end of the indwelling feeding tube, such as with a syringe, but a good connection and accurate administration is not possible. The open end of the typical indwelling feeding tube has a port shaped like the inside of a cone. It is made to accommodate the nozzle tip of the tubing set of a standing reservoir. The port is made of flexible, rubbery plastic material, and the tip of an e.g. irrigation syringe can be forced into the port to get some purchase. This is not leak proof, however. Newer feeding tubes have a Y-port, said to be for irrigation and administration of medications. However, the addition of another similarly shaped port does not provide a means for making a more secure attachment to the port, to prevent leaks or stabilize the apparatus.

Home-bound patients on enteral feeding solutions(with a feeding tube still in place) are instructed to hold the tip of a 60 ml syringe barrel in the port, and pour feeding solution into the syringe barrel. This delivery arrangement is barely adequate for the patient who must attend the feeding, and inappropriate for nursing staff. In addition, it lacks the leak-proof seal, clamp and drip chamber generally used to oversee the correct administration of medications.

Examples of tubing sets for enteral feeding using a feeding pump are the Ross Medical Nutritional Products Pump and Gravity Set with Piercing Pin, and the Ross Nutritional Enteral Pump Set with Piercing Pin for use with a non-Ross Pump. Both tubing sets comprise a piercing pin to connect to a pin port provided on a feeding solution bag or reservoir. The piercing pin is connected to a tubing path with a drip chamber and roller clamp disposed along the path of the tubing, and having a nozzle shaped connector at its distal end, for attachment to the port indwelling feeding tube. Other tubing sets are made with a threaded aperture in place of the pin. The feeding solution container used with this tubing set has a threaded opening. Though a wide variety of tubing sets are commercially available, none are provided with means for attaching to a dosage vessel, such as a syringe, needed to accurately administer medications to the indwelling feeding tube. In addition, commercially available enteral feeding containers are not good dosage vessels. Their large reservoir size makes them inappropriate for administration of small volumes of medications, as the medications coat the inner wall of the container, leaving a portion of the dose unadministered.

Medications are not typically packaged in small volume containers that can be accessed with a tubing set. Without the proper connectors, the attachment to the feeding tube will be unstable, and the nurse required to hold the connection to stabilize it. An accidental destabilization or disconnnect will create a leak, leaving the nurse with the knowledge that some medication was given but not knowing how much. It may not be possible to correct for the misadministration. Even with considerable effort, the unstable connection may make it impossible to complete the administration of the dose. Placing another tube in the patient is not the solution.

U.S. Pat. No. 5,527,280 illustrates a gastric or stomach feeding tube for placement through an abdominal stoma into the stomach, and a narrow jejunal feeding tube which passes through the gastric tube. The gastric feeding tube is fixed in position with the distal end held within the stomach by balloon. Gastric feeding is administered through the internal bore of the gastric tube. A narrow jejunal feeding tube may be threaded through the gastric feeding tube to the small intestine. This device is designed to permit a transition from gastric to jejunal feeding without having to insert a jejunal tube alongside the gastric tube. The trade-off is in the larger overall diameter of the stoma for inserting this large bore device, but this is considered superior to creating the irregularly shaped stomal opening needed for side-by-side tubes.

The device is also described as a feeding and medicating device, the gastric tube being available for administering medications after the jejunal tube is extended for feeding. After switching from gastric to jejunal feeding, the lumens are in position to introduce medications through the gastric tube openings. Jejunal feeding rates, however, are so much slower than stomach feeding rates that the switch would not be made simply for alternate delivery routes for oral medication. In addition, the ports for the gastric and jejunal tubes are constructed for attachment to the enteral feeding tubing set, and have no means for connecting a small dosage vessel. Thus, though a variety of lumens are offered by the device, none provide adequate means for intermittently administering medications through the feeding tube.

U.S. Pat. No. 5,071,405 illustrates a single lumen multiport abdominal stomal feeding tube. The feeding tube has three ports. One is the main inlet port for enteral feeding solution. Another, is the Y-port, for the administration of medications, and for gastric suction, if needed. The last port is provided to inflate/deflate a balloon which abuts the skin about the stoma, anchoring the device against the skin. The Y-port, has a plug for use when the lumen is not in use. In terms of structure, this device is similar to simply adding a Y-port at the open end of the indwelling feeding tube. While the Y-port appears to offer a method for delivering medications while feeding, in use, it is very time consuming and difficult to administer medications through the Y-port. As with adding medication to a container of enteral feeding solution, administration time is slowed by being combined with the feeding solution in the tube. In addition, difficulties in feeding may affect the quantity and timing of the administration of medications. In addition multiple ports provide multiple access points for possible contamination, requiring repeated cleaning. Providing multiple ports provides no teaching or suggestion of what is needed to attach to the port, namely a dosage vessel with a secure fluid path, which can be firmly and reliably attached to the port of a feeding tube, to accurately deliver a dose of medication. Thus the need still remains for a stable, secure connection for administering medications to a patient through an indwelling enteral feeding tube.

Use of the apparatus of the present invention provides a number of advantages. When a nurse has to administer a number of medications, the liquid medications are poured into and accumulated in the dosage vessel, and administered into the open port of an indwelling feeding tube. In addition, the nurse may either cap the vessel, or mount the apparatus, or both, quickly eliminating the danger of unsecured or mis-administered medications. The apparatus of the present invention permits the nurse to make a secure attachment to the open port of the feeding tube, and remove both hands from the attachment. If filling the dosage vessel at the bedside, the nurse has both hands free to place medications and/or food into the dosage vessel, and correctly and accurately administer the necessary medications and/or food. In addition, she may attach the apparatus, and then have both hands free to open a can of feeding solution.

SUMMARY OF THE INVENTION

The present invention provides an apparatus for the accurate feeding of medications, to the indwelling feeding tube of a patient on enteral feeding. The apparatus has a small dosage vessel connected to a secure fluid path, which makes a fluid-tight connection to the open end of an indwelling feeding tube. The dosage vessel may have a top opening for adding medications to the vessel. After adding the medication, a fluid tight cap may be placed over the top opening, if desired. In another preferred embodiment the vessel may be sealed to form a sealed chamber containing a pre-measured dose. The dosage vessel or sealed chamber may have a volume of from about 25 milliliters to 250 milliliters, and preferably from about 50 to about 100 milliliters. Preferably the vessel or chamber bears lines of volume gradation, so that the nurse may monitor the volume of medications administered from the vessel or chamber. It is also preferred that the cap have means such as a hanging ring with which to mount the apparatus to a stable mounting.

At the distal end of the fluid path is a feeding tube connector for making a stable attachment to the indwelling feeding tube. Intermediate the vessel and the connector, the tubing passes through 1) means for regulating the fluid flow, such as a roller clamp, which may be adjusted to stop, establish or restrict the fluid flow through the tubing, and 2) a drip chamber, or other means to display the rate of flow, may be located intermediate the roller clamp and the dosage vessel. The means for regulating the flow must include means to stop the flow to fill the vessel, or stop the administration of the medication, means to re-establish flow, and means to restrict flow for observation of the flow rate in the drip chamber. The apparatus of the present invention permits a nurse to easily and safely provide medications to a patient with an indwelling enteral feeding tube. In a preferred embodiment, the dosage vessel is similar to a syringe barrel, and it is formed integrally, or securely attached, with a drip chamber. The present invention also comprises a method for administering medications, and bolus feedings using the apparatus of the present invention.

DETAILED DESCRIPTION OF THE INVENTION

Figure 1:
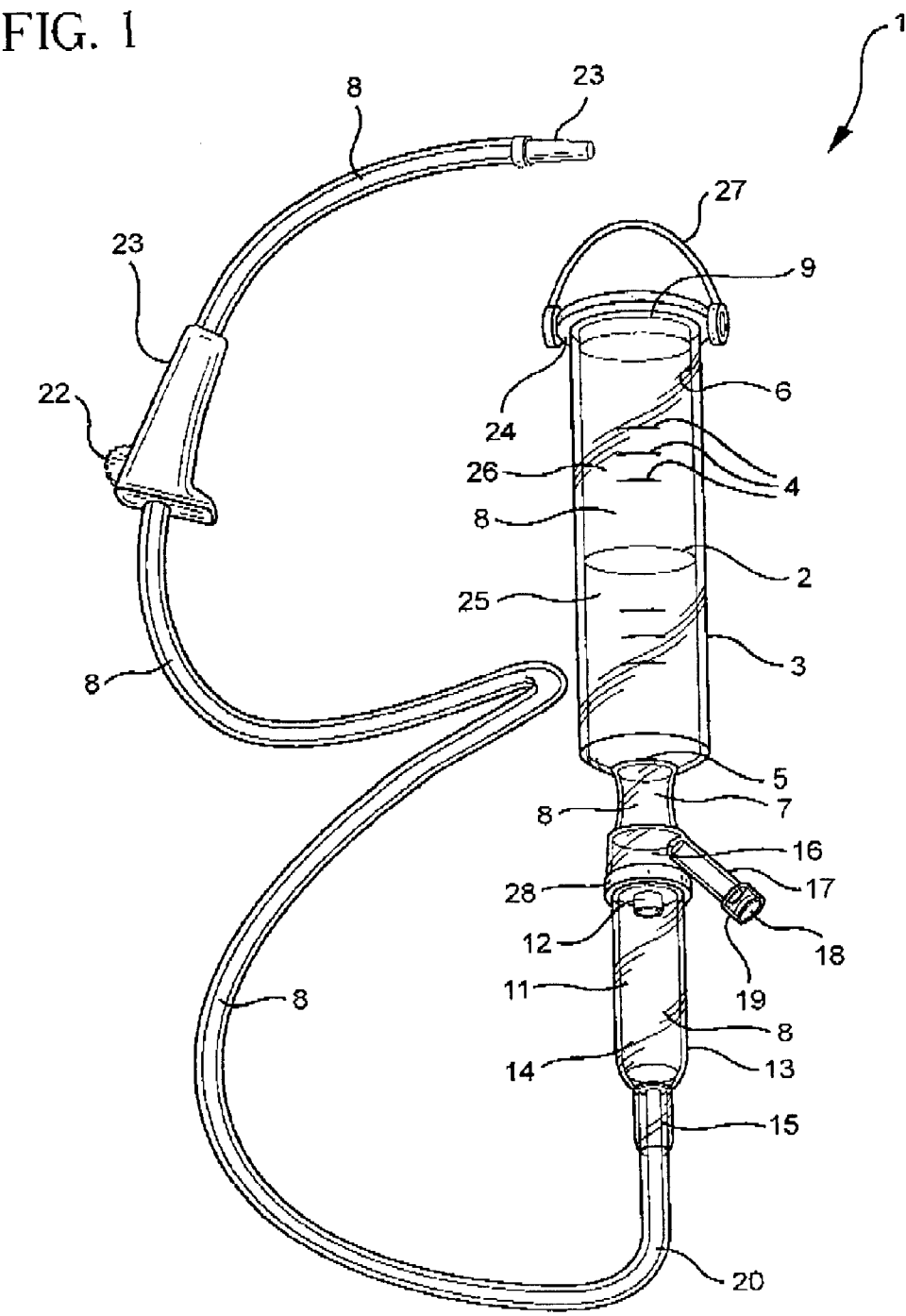
FIG. 1 is a prospective view of a preferred embodiment of the apparatus of the present invention, containing a pre-measured dose, and showing a preferred cap for the dosage vessel.

A preferred embodiment of the apparatus of the present invention is shown generally at 1 in FIG. 1. It comprises a dosage vessel 2 with a volume of from 25 milliliters to 250 milliliters. In this preferred embodiment, the dosage vessel 2 is cylindrical in shape and bears gradation lines 4 to indicate the fluid volume in the vessel 2. As shown, the dosage vessel 2 has a top opening 9 and at least one (cylindrical) wall 3. It is not necessary that the vessel 2 have one wall, and a cylindrical shape is not required, though this shape has been traditionally preferred for the administration of liquids. The barrel of syringe provides an excellent cylindrical shape which easily accommodates a plunger to perform the steps of 1) confirming proper placement of the feeding tube, 2) removing the volume of feeding solution remaining in the tube and stomach from the last feeding, and 3) irrigating the feeding tube with water after administration of feeding or medication. Preferably, the wall(s) 3 of the vessel 2 are formed of rigid material, but flexible vessels are also contemplated by the present invention.

The vessel wall(s), 3, have an inner surface, 6, in fluid communication with a drain, 5, which abuts the lower portion of the wall(s). A drain passageway, 7, is securely attached to the vessel drain, 5. The drain passageway is securely attached to the remainder of the fluid path, 8, yielding a secure fluid path from the dosage vessel to the feeding tube. To form the secure attachment, the parts may be integrally formed, or permanently secured, or provided with an e.g. leak-proof snap on or other secure attachment means. As shown, the fluid path comprises known elements of a tubing set, namely, an air vent, 16, a drip chamber, 11, and tubing 20 with clamp 21. The distal end of the tubing has a connector, 23, to create a secure connection to the indwelling (in place in the patient's stomach) feeding tube. The connector may be made by, e.g., a threaded connection, or typically, a cone shaped, nozzle connector, shown at 23, at the end of the tubing, 20.

FIG. 1 illustrates a preferred embodiment of the apparatus of the present invention, with a pre-measured dose, 25, secured under a cap, 24. The vessel can be used without the cap, 24, leaving an open top, or the cap, 24, may be placed on the vessel, after the medication has been added to the vessel. Preferably, the cap snaps into the top opening, 9, which remains fixed therein until removed, to create a fluid tight seal in the opening. If desired, a cap may be permanently sealed to the opening, creating a tamper-proof sealed chamber, 26. In the preferred embodiment the cap bears means, 27, such as a hanging ring, for making a stable mounting, to e.g. an iv pole. Without secure attachment of drain passageway, 7, to the remainder of the fluid path, accidental jostling of the apparatus may de-stabilize the apparatus, making it difficult to use, and in the most extreme case, may create a fluid leak.

A means for establishing, regulating and ending fluid flow from the dosage vessel, 2, to the connector, 23, such as a roller clamp, 21, is located intermediate the open dosage vessel or closed chamber 2, and tubing connector, 23. The tubing extends between the roller clamp 21 and its rotatable wheel, 22 The rotatable wheel, 22, is connected to the clamp in such a manner that turning the wheel moves it toward or away from the tubing so as to adjust the volume, turn the flow off, and re-establish flow. This permits the nurse, or care giver, to stop, or adjust, the administration of medications from the dosage vessel or closed chamber. In addition, this permits the nurse to move about the patient, or leave the bedside in case of an emergency elsewhere. Lastly, the ability to turn off the flow and re-establish flow at the roller clamp, permits the nurse, or the pharmacist, to pre-fill the vessel at the nursing station or in the pharmacy.

Intermediate the dosage vessel 2 and the roller clamp 21 is a means for displaying the flow through the device, which may comprise a typical drip chamber 11. The drip chamber 11 has a drip port 12, a cylindrical wall 13, and an egress port 15 which define the drip chamber reservoir 14. The size of the drip chamber reservoir 14 and the flow rate are such that fluid does not completely fill the drip chamber reservoir 14, but drips from drip port 12 to give a visual indication of the rate of flow through the clear walls of the drip chamber 11. When the drip chamber 11 is constructed of flexible, resilient material, e.g. plastic, the wall 13 of the drip chamber 11 may be pinched to create a back flow through the drain, to dislodge any particulates which may accumulate in the vessel drain 5 as the dose flows into the passageway 7.

In the preferred embodiment shown in FIG. 1, an inverted-Y, one-way air vent, 16, may be located between drip chamber and the dosage vessel. An example of the structure of a one-airway vent is shown at 16, in FIG. 2. The vent is formed of a side arm, 17, which provides an air passageway in communication with the dosage vessel. A ball, 17a, is seated in socket, 17b, created in the side arm. This one-way vent permits air to enter the dosage vessel through the side arm, 17, but prevents fluid flow from the side arm to the vessel. The side arm, 17, has a cap, 19, which when placed on the side arm disposes an air permeable membrane, 18, across the opening of the side arm. The apparatus is thus air-vented but fluid travel into or out of the arm is prevented.

Figure 2:
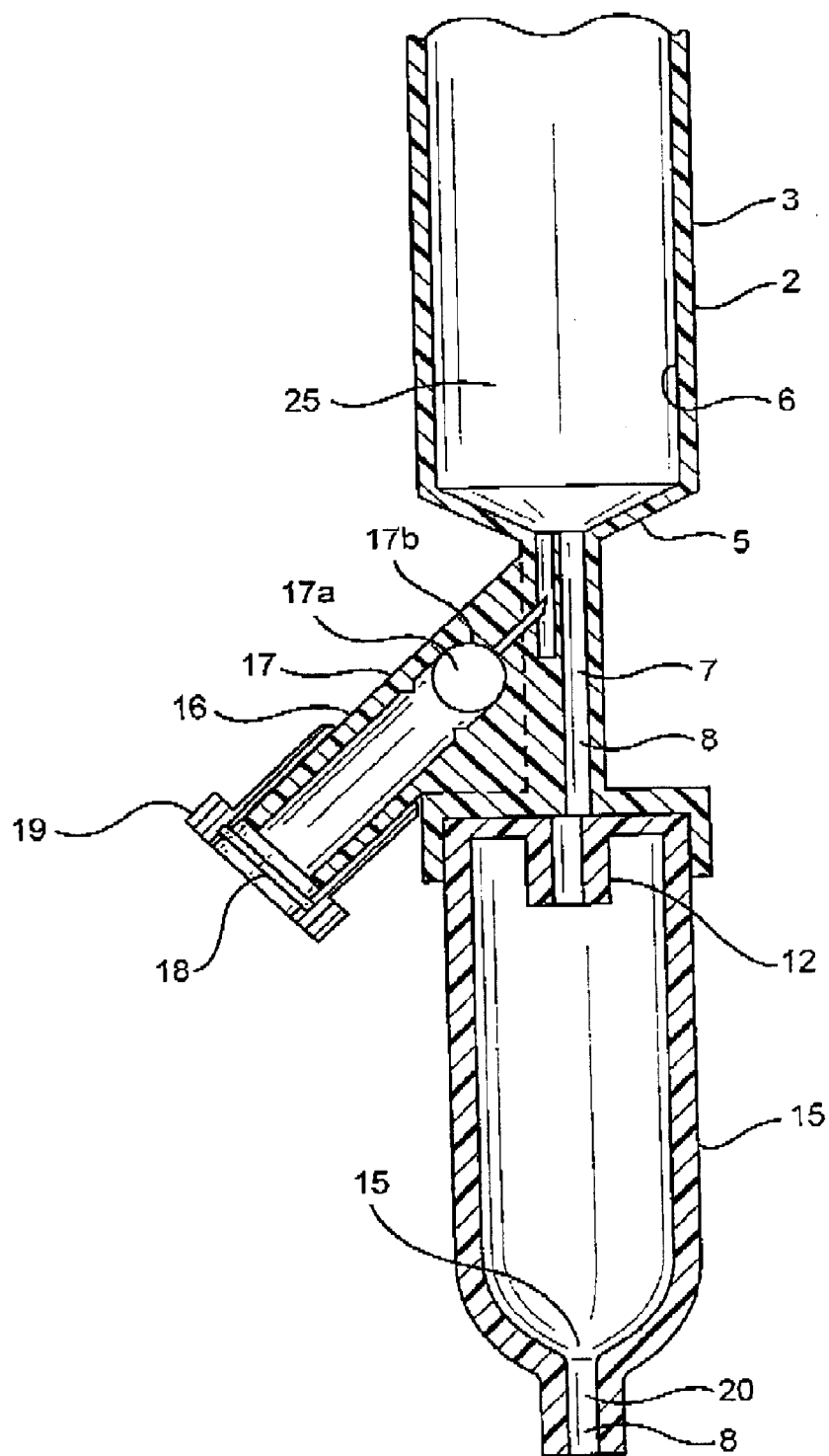
FIG. 2 is a lengthwise cross-sectional view of a preferred embodiment the apparatus of the present invention.
Figure 2A:
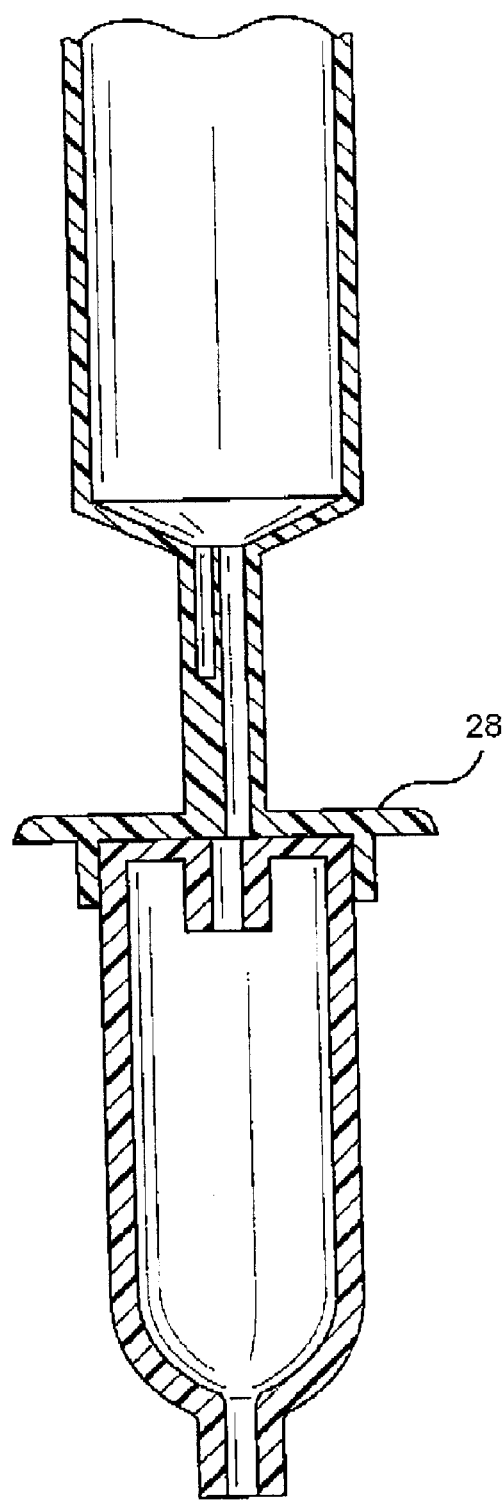
FIG. 2A is a lengthwise cross-sectional view of the apparatus depicted in FIG. 2, viewed at a 90 degree rotation about the length of the apparatus.

FIG. 2A illustrates the apparatus of FIG. 2, rotated 90° about its length wise axis. Shoulders 28, shown in perspective view in FIG. 1, are more clearly shown in FIG. 2A. The shoulders facilitate gripping the drip chamber, and the whole apparatus.

In use, the apparatus of the present invention provides a number of advantages. When a nurse has to administer a number of medications, the separate cups or containers are usually placed on a tray and taken to the patient's bedside. Sometimes, the liquid medications are poured into, e.g., a 30 ml. cup, or directly into the dosage vessel and administered to the patient. Powdered medications are then mixed with water and administered to the patient. The medications are placed in a syringe, and the nose of the syringe forced into the open port of the feeding tube. However, the engagement between the syringe and port is not strong, and may at any moment require two hands to stabilize. Even if the nurse is momentarily comfortable holding the syringe in the port with one hand, if a can of feeding solution has been left unopened, the nurse does not have two hands free to open it. The nurse may not leave the patient's room before all the medications are administered, as unsecured and unlabeled medications constitute an unacceptable danger. The apparatus of the present invention permits the nurse to assemble the medications in the dosage vessel 2, and either cap the vessel 2, or mount the apparatus, or both, quickly eliminating the danger of unsecured or mis-administered medications. In addition, once the nurse has made a secure attachment of the tubing connector to the open port of the indwelling feeding tube, there is no more requirement to hold the connection. Thus the nurse has both hands free to attend to the administration of medications and/or food.

Because the vessel drain is securely attached with the drain passageway, which is securely attached to the remainder of the fluid path, and the nurse does not have to hold the connection, nor attempt to stabilize it, as with adhesive tape. Taped connections are not fluid tight, and leave adhesive residue on the connectors and tubing ends. The adhesive residue may interfere with subsequent attempts to connect a dosage vessel, or to reconnect the trailing end of the in feeding tube extending from the feeding solution reservoir or pump.

With the vessel securely attached to the drain passageway and the remainder of fluid path tubing, the nurse can hold the vessel in one hand, and apply to pressure to cap the top opening of the vessel without concern for breaking the seal between the drain passageway and the remainder of the flow path. In addition, the secure attachment of the parts, permits the use of a single means, 27, for securing the apparatus to a stable mounting, such as a IV pole, can be used without risking the fluid seal between the vessel and the fluid path.

Measuring and administering the correct volume of medication may be accomplished by reference to gradations, 4. When administering powdered medications or crushed tablets, they are mixed with water, placed in the dosage vessel and administered therefrom. Should the fluid path become blocked, the nurse may squeeze the drip chamber, 11, to dislodge any particulates which may have settled at the drain, 5, of the open dosage vessel or closed chamber.

Air entering the side arm of the vent travels to the vessel to replace the fluid volume of the administered dose, and thereby assist in draining fluid from vessel. If administration of the dose needs to be attended, the fluid flow may be stopped if the nurse should need to leave the bedside. Following administration of the dose, the apparatus may be disconnected from the indwelling feeding tube, which may then be flushed, as with an irrigation syringe, and reconnected to the connection on the tube trailing from the feeding solution reservoir or pump.

To begin administration of the medication, the tubing set is disconnected from the indwelling feeding tube. An irrigation syringe is then used to confirm placement of the distal end of the feeding tube, by pushing air or liquids into the tube. Tubing connector, 23, may then be attached to the open end of the indwelling feeding tube Fluid flow is established from the dosage vessel to the indwelling feeding tube by flow regulator means, such as clamp, 21. After administering the dosage with the apparatus of the present invention, tubing connection, 23, is disconnected from the feeding tube and the feeding tube is flushed and reconnected to the trailing end of the tube from the feeding solution reservoir or pump. Thus the carefully placed enteral feeding tube is used and not dislodged, and easily reattached to reservoir or pump feeding tube. As a general estimate, at least 100 ml of water is required for flushing the feeding tube before and after administration of medication.

In the method of the present invention, the dose may be added to the vessel at the bedside, the nurses station, or the pharmacy. Some doses are a fixed volume, while others, such as a fixed amount of a powdered medication stirred in water are of variable volume. Filling the dosage vessel requires, first, turning off the fluid flow through the fluid path, such as with a roller clamp, 21, operated by rotating wheel, 22. After adding the dose to the vessel, the vessel may be left open, capped and/or sealed to form a fixed dose sealer chamber. While the feeding pump may also have means for interrupting or regulating the fluid flow, retaining the dose in the vessel requires that a flow regulation means is connected to the apparatus. After connecting the tubing connector, 23, to the open end of an indwelling feeding tube, flow can be initiated, and regulated, as by opening the clamp.

The arrangement of the various elements of the fluid path are presented herein in there preferred order and structure, but other orders of the e.g., vent, drip chamber and clamp are possible along the fluid path. The apparatus of the present invention may also find use in administering bolus feeding into an indwelling tube. In this use, the addition of the means for making a stable mounting lets the nurse move about the bed side to attend to other nursing care needs, during administration of the bolus. For patients sent home with an indwelling feeding tube the apparatus of the present invention permits bolus administration of feeding solution with the convenience of a cap and mounting means, as well as the fluid-tight fastening of the apparatus into the feeding tube.

While there have been described what are presently believed to be the preferred embodiments of the present invention, those skilled in the art will realize that changes and modifications may be made thereto without departing from the spirit of the invention. It is intended to claim all such changes and modifications as fall within the true scope of the invention

What is claimed is:

1. An apparatus for administering medications to a patient with an indwelling enteral feeding tube, said apparatus comprising,
    a dosage vessel comprising at least one wall with an inner surface abutting a drain, said dosage vessel having a volume of from about 25 milliliters to about 250 milliliters, said at least one wall defining a top opening enabling fluid to be directed into said dosage vessel via said top opening in its entirety when said top opening is uncovered, and
    a leak-proof secure fluid path from the dosage vessel to the feeding tube, said fluid path comprising
    a drain passageway securely attached to said drain,
    a drip chamber securely attached to said passageway, said drip chamber having a top portion with a drip port, a bottom portion with an egress port and a cylindrical wall extending therebetween and defining a drip chamber reservoir,
    tubing securely attached to said drip chamber egress port and forming a fluid path therefrom to the feeding tube, said tubing comprising a tubing connector for making a secure attachment to the feeding tube,
    regulating means for regulating the fluid flow from said dosage vessel to the feeding tube;
    an air vent to said dosage vessel in said fluid path, intermediate to said drain and said drip chamber;
    a membrane disposed across said air vent; and
    a cap releaseably placed over said air vent.

2. The apparatus of claim 1, wherein said dosage vessel further comprises means for measuring the volume of a liquid in said dosage vessel.

3. The apparatus of claim 1, wherein said dosage vessel is a sealed chamber containing a pre-measured dose.

4. The apparatus of claim 1, further comprising a cap arranged to snap into and cover said top opening defined by said at least one wall.

5. The apparatus of claim 1, wherein said dosage vessel further comprises mounting means for mounting said dosage vessel to an I.V. pole.

6. The apparatus of claim 1, wherein said drip chamber is formed of a flexible, resilient material.

7. The apparatus of claim 1, wherein said passageway is permanently attached to said drain.

8. The apparatus of claim 1, wherein said dosage vessel has a volume of from about 50 ml. to about 100 ml.

9. The apparatus of claim 1, wherein said regulating means comprises a roller clamp on said tubing, located between said drip chamber and said tubing connector.

10. The apparatus of claim 3, wherein said at least one wall of said sealed chamber is made of flexible material.

11. The apparatus of claim 4, wherein said cap further comprises mounting means for mounting the apparatus to an I.V. pole.

12. A method for accurately administering medications into an indwelling feeding tube, comprising the steps of,
    providing an apparatus as in claim 1,
    securely connecting a distal end of the tubing to the feeding tube,
    adjusting the regulating means to stop the flow in the fluid path,
    placing at least one dose of medication in the dosage vessel,
    adjusting the regulating means to initiate and regulate the rate of administration of the dose.

13. The method of claim 12, further comprising the step of sealing the dose in the dosage vessel to create a sealed chamber with a pre-measared dose.

14. The method of claim 13, further comprising opening the air vent as required to ensure fluid flow from the sealed chamber.

15. The method of claim 12, further comprising the step of measuring the volume of dose added to the dosage vessel, or drained from the vessel, using volume markings provided on the at least one wall.

16. The method of claim 12, further comprising the step of monitoring the administration of a dose using the volume markings on the vessel wall.

17. The method of claim 12, wherein the apparatus further comprises a cap arranged to snap into and cover the top opening of the dosage vessel, and the method further comprises capping the dosage vessel after placing the medications in the vessel.

18. The apparatus of claim 1, further comprising a cap arranged to contact said at least one wall and seal said top opening.

19. The apparatus claim 1, further comprising an air vent leading to said dosage vessel and arranged between said drain and said drip chamber, said air vent being arranged alongside said passageway.

20. The apparatus of claim 19, wherein said air vent is arranged under or below said drain.

21. The apparatus claim 1, further comprising an air vent leading to said dosage vessel, and arranged between said drain and said drip chamber, said air vent being arranged under or below said drain.

22. An apparatus for administering medications to a patient with an indwelling enteral feeding tube, comprising:
a dosage vessel comprising at least one wall with an inner surface abutting a drain, said dosage vessel having a volume of from about 25 milliliters to about 250 milliliters;
a leak-proof secure fluid path from said dosage vessel to the feeding tube, said fluid path comprising
a drain passageway securely attached to said drain,
a drip chamber securely attached to said passageway, said drip chamber having a top portion with a drip port, a bottom portion with an egress port and a cylindrical wall extending therebetween and defining a drip chamber reservoir,
tubing securely attached to said egress port and forming a fluid path therefrom to the feeding tube, said tubing comprising a tubing connector for making a secure attachment to the feeding tube, and
regulating means for regulating the fluid flow from said dosage vessel to the feeding tube;
an air vent to the dosage vessel in the fluid path, intermediate to said drain and said drip chamber;
a membrane disposed across said air vent; and
a cap releaseably placed over said air vent.

23. A method for accurately administering medications into an indwelling feeding tube, comprising the steps of:
providing an apparatus comprising a dosage vessel comprising at least one wall with an inner surface abutting a drain, a leak-proof secure fluid path from the vessel to the feeding tube, the fluid path comprising a drain passageway securely attached to the drain, a drip chamber securely attached to the passageway, the drip chamber having a top portion with a drip port, a bottom portion with an egress port and a cylindrical wall extending therebetween and defining a drip chamber reservoir, tubing securely attached to the egress port and forming a fluid path therefrom to the feeding tube, and regulating means for regulating the fluid flow from the vessel to the feeding tube;
securely connecting the distal end of the tubing to the feeding tube;
adjusting the regulating means to stop the flow in the fluid path;
placing at least one dose of medication in the vessel;
adjusting the regulating means to initiate and regulate the rate of administration of the dose;
sealing the dose in the vessel to create a sealed chamber with a pre-measured dose;
providing a closeable air vent to the sealed chamber; and
opening the air vent as required to ensure fluid flow from the chamber.

\* \* \* \* \*